US010998088B2

(12) United States Patent
Lo Priore (10) Patent No.: US 10,998,088 B2
(45) Date of Patent: May 4, 2021

(54) METHOD FOR MANAGING THE PROTOCOLS USED BY DEVICES FOR DIAGNOSTIC AND CLINICAL ANALYSIS AND RESULTS OBTAINED FROM SUCH DEVICES

(71) Applicant: HYRIS LIMITED, London (GB)

(72) Inventor: Stefano Lo Priore, Lugano (CH)

(73) Assignee: HYRIS LIMITED, London (GB)

( * ) Notice: Subject to any disclaimer, the term of this patent is extended or adjusted under 35 U.S.C. 154(b) by 335 days.

(21) Appl. No.: 15/534,622

(22) PCT Filed: Dec. 11, 2015

(86) PCT No.: PCT/IB2015/059553
§ 371 (c)(1),
(2) Date: Jun. 9, 2017

(87) PCT Pub. No.: WO2016/092521
PCT Pub. Date: Jun. 16, 2016

(65) Prior Publication Data
US 2017/0364652 A1    Dec. 21, 2017

(30) Foreign Application Priority Data

Dec. 11, 2014    (IT) .............................. RM2014A0715

(51) Int. Cl.
*G16H 10/40* (2018.01)
*G16H 40/67* (2018.01)
*G16H 80/00* (2018.01)
*A61B 5/00* (2006.01)

(52) U.S. Cl.
CPC ............. *G16H 10/40* (2018.01); *G16H 40/67* (2018.01); *A61B 5/7275* (2013.01); *G16H 80/00* (2018.01)

(58) Field of Classification Search
None
See application file for complete search history.

(56) References Cited

U.S. PATENT DOCUMENTS

| 2011/0289442 | A1* | 11/2011 | Abrams ................. G16H 10/40 |
| | | | 715/771 |
| 2012/0166211 | A1* | 6/2012 | Park ...................... G06F 19/321 |
| | | | 705/2 |
| 2013/0079599 | A1* | 3/2013 | Holmes ............... G06F 19/3418 |
| | | | 600/300 |
| 2013/0125158 | A1* | 5/2013 | Brown .................. G06Q 30/02 |
| | | | 725/14 |

FOREIGN PATENT DOCUMENTS

| WO | 2008051310 | 5/2008 |
| WO | 2014055963 | 4/2014 |

OTHER PUBLICATIONS

International Search Report and Written Opinion for International Patent Application PCT/IB2015/059553 dated Jan. 3, 2017.

* cited by examiner

*Primary Examiner* — Cai Y Chen
(74) *Attorney, Agent, or Firm* — Hunton Andrews Kurth LLP (57) ABSTRACT

The present invention relates to a method for the management of the protocols used by devices for clinical-diagnostic analyses and the results obtained by said devices. The present invention further relates to the systems apt to perform such method.

20 Claims, 6 Drawing Sheets

METHOD FOR MANAGING THE PROTOCOLS USED BY DEVICES FOR DIAGNOSTIC AND CLINICAL ANALYSIS AND RESULTS OBTAINED FROM SUCH DEVICES

CROSS REFERENCE TO RELATED APPLICATIONS

This application is a U.S. National Phase of International Patent Application PCT/IB2015/059553, filed Dec. 11, 2015, which claims priority to Italian Patent Application No. RM2014A000715, filed Dec. 11, 2014, the disclosure of each of which are hereby incorporated by reference.

The present invention relates to a method for the management of the clinical protocols apt to run on devices for clinical and diagnostic analysis and the results obtained by said devices. The present invention further relates to the systems apt to perform such method.

In the analysis laboratories often there is a plurality of devices, each one connected to a different computer. Each single computer stores both the clinical protocols which are performed by the instrument and the results of the specific test performed by the device.

In the state of art, in order to centralize the filing of the results, the single computers often are connected to a central server by means of a local network. However, the configuration shown in the state of art has several disadvantages.

The diagnostic devices which have been currently used in the state of art have still a 'closed' configuration, meaning that both the loading of the parameters of the clinical-diagnostic test to be formed and the storing and transmission of the test results are performed by means of a computer which physically lies in the site wherein the analysis takes place, or by means of inputting the parameters by an operator. Even if during the normal operation in a laboratory environment this is not a disadvantage, as the computerized system of the laboratory provides the required network functionality, it becomes a disadvantage in other types of systems.

For example in a scenario of decentralized tests, wherein the access to an infrastructure for managing existing data is not readily available, such limitation is a constraint which slows down and makes less efficient the management of the clinical protocols and of the results of analyses.

The U.S. patent application US2013/079559 discloses systems and methods for providing results of diagnostic analyses. Such methods and systems, differently from the present invention, provide that the transmission of the clinical protocols between diagnostic devices and the mobile device is direct and then not mediated by a server.
Such problem is solved by a method according to claim 1, even a system according to claim 8 is subject of the present invention.

The method according to the present invention allows any user of the system to access a 'virtual laboratory' including the units which perform the analysis tests and the software associated to the central servers at an extremely low cost.

The method according to the present invention further allows to collect the most useful data, since in a traditional laboratory test all samples first of all are brought to the laboratory, with a probable information loss connected to the time and place of the analysis (which may require additional steps of preservation which not always can be possible in all environments). Therefore, the possibility of errors by the operators in the field is reduced drastically, since they no more have to be concerned about the correctness of the protocol parameters, the collection, the storage and the transmission of the test results.

Preferred features of the subjects of the present invention are shown in the depending claims.

Additional advantages, as well as the features and the operating steps defining the present invention will result evident from the following detailed description related to the possible embodiments thereof, shown by way of example and not for limiting purposes.

Figure 1:
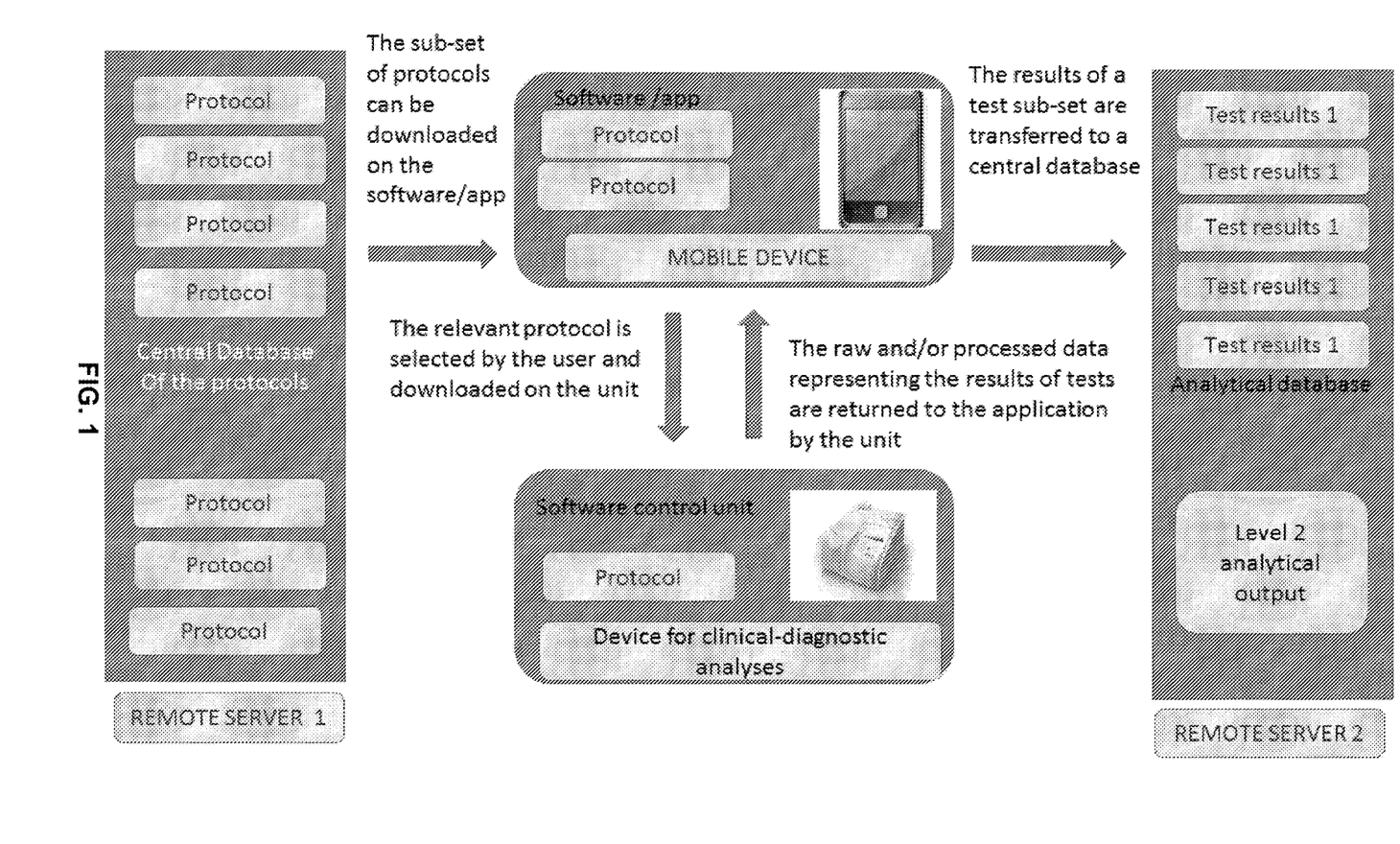
FIG. 1 is a flow chart schematizing the operating steps of an embodiment of the method according to the present invention.
Figure 2:
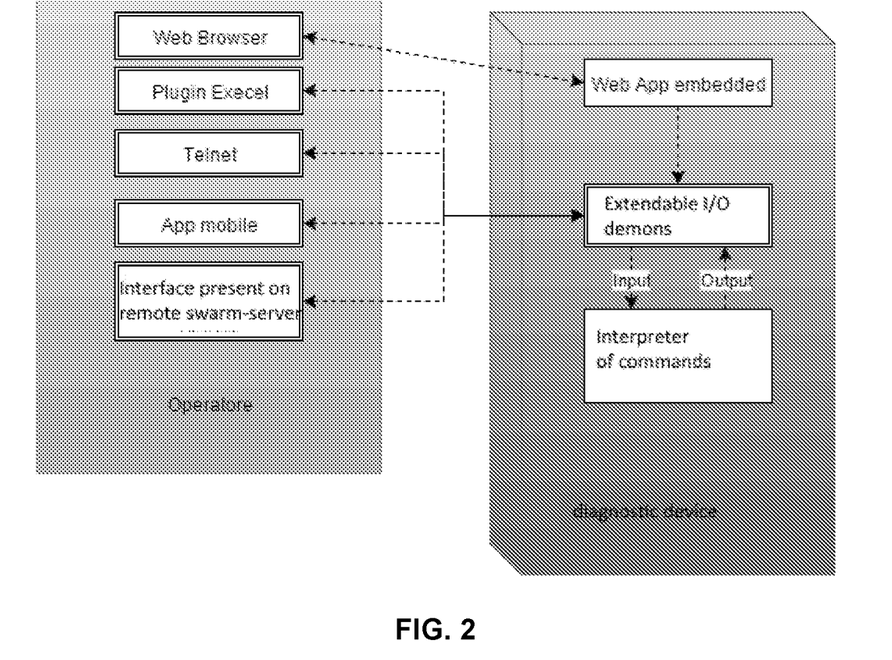
Figure 3:
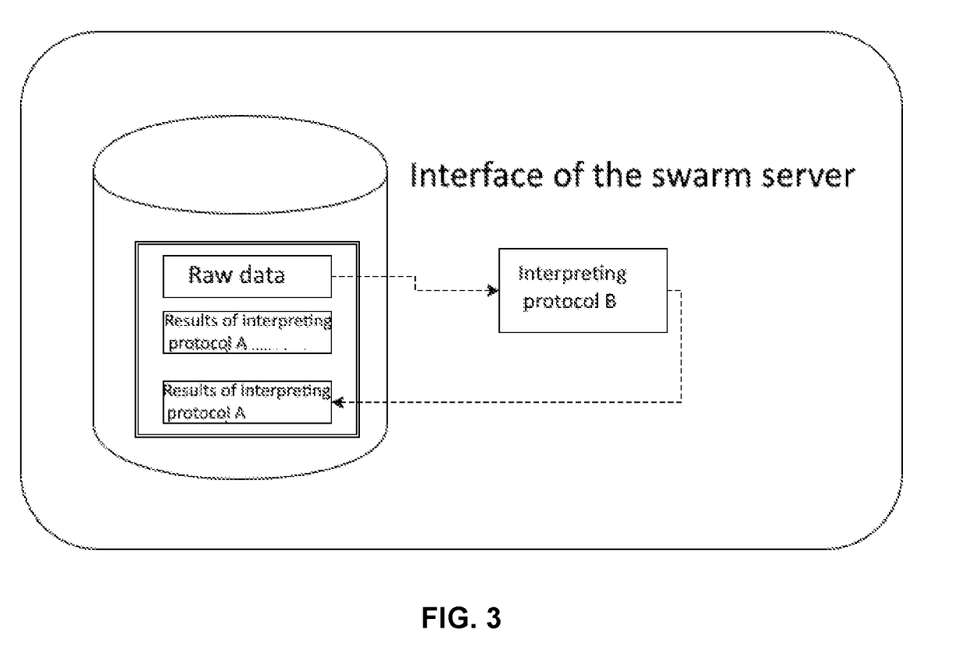
Figure 4:
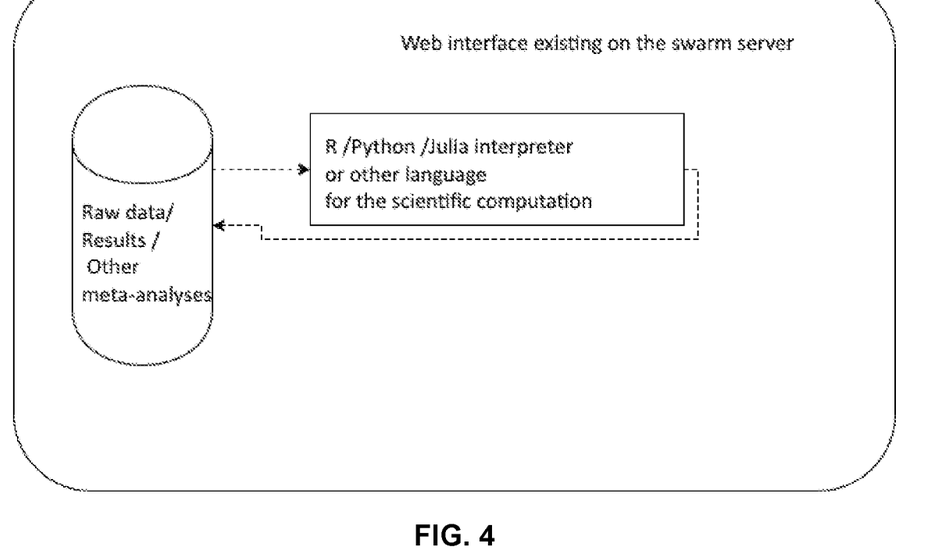
Figure 5:
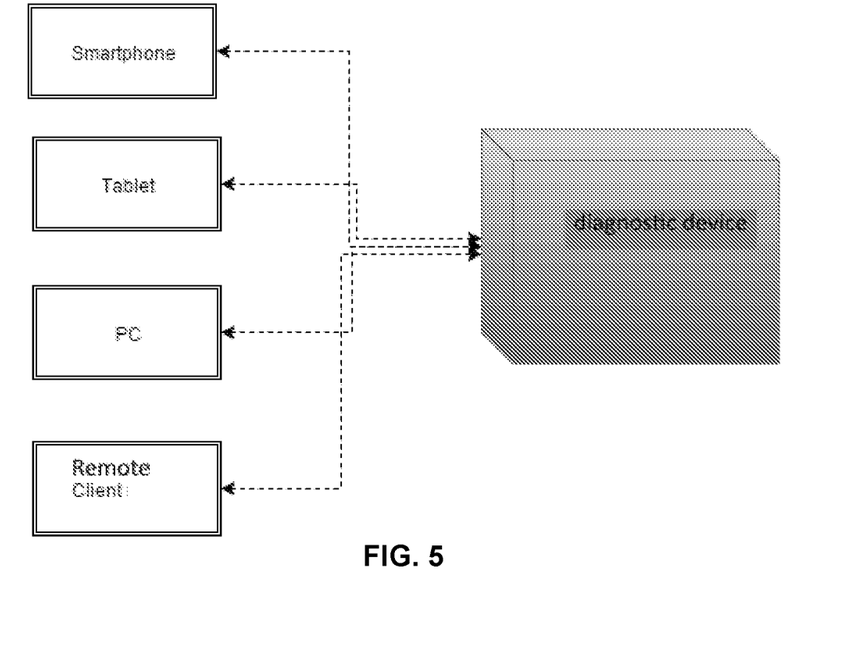
Figure 6:
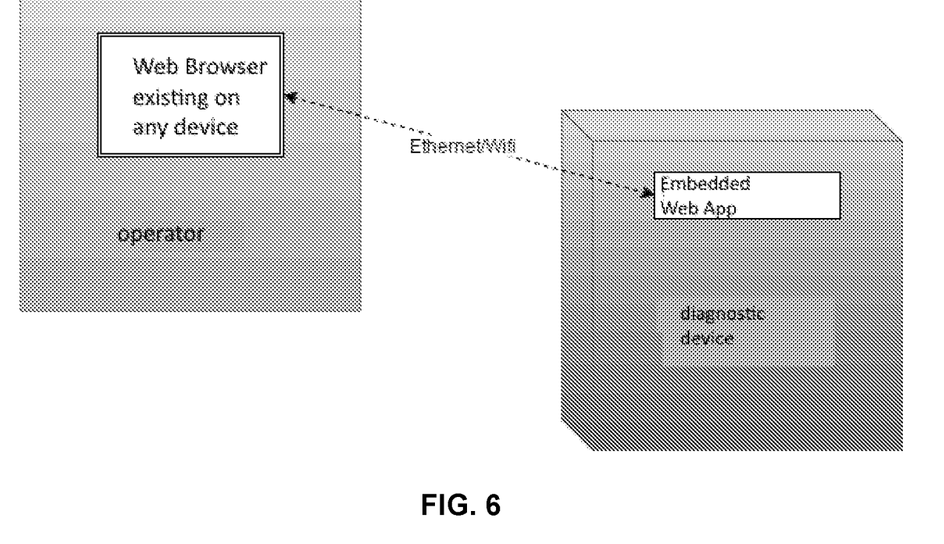

The method according to the present invention relates to the management of the clinical protocols which are used by the different devices existing in the laboratories to perform analyses of clinical or diagnostic type and to the management of the results of the analyses produced by such devices.

The first passage a) of the method provides to store on a first remote server a plurality of clinical protocols apt to run on the devices for clinical-diagnostic analyses, according to an embodiment such server could be programmed for filing and updating all parameters required to perform an analysis and be programmed for providing the access to data limited to specific classes of users. In the second passage b) one or more of the clinical protocols stored on the server are transmitted to a mobile device, such as for example a tablet or a smartphone. The connectivity provided by the portable device, for example by means of wireless networks, guarantees that the clinical protocols are discharged on the software existing on the mobile device which could be updated periodically so that whenever an analysis is performed the correct protocol could be used.

In the passage c) the clinical protocols are transmitted from said mobile device to a device for clinical-diagnostic analysis suitable to receive and perform the sent clinical clinical protocols, for example a device for clinical-diagnostic analyses comprising a personal computer and an apparatus for analyses of rtq PCR or PCR lamp.

In the passage d) a clinical-diagnostic analysis according to the protocol transmitted at point c) is performed, whereas in the passage e) the analysis results are transmitted from the device whereon the analysis was performed to the mobile device.

In the passage f) then the results are transmitted from the mobile device to a second remote server, according to a preferred embodiment the first and second server could coincide.

The invention then provides the creation of a centralized file of clinical protocols, which are managed centrally, such file could be downloaded/updated in real time even remotely for example by using a remote access by means of Internet. According to a specific configuration the clinic protocols and/or the stored results could be modified and/or displayed only by authorized users, so as to guarantee a higher safety of the system.

According to an embodiment the data transmitted in the various passages of the method are transmitted through the Internet networks and/or Intranet networks of wireless type, for example by means of email, sms, instant messaging services and/or applications for smartphone. Preferably the transmitted data will be encrypted according to anyone of the methods known to the person skilled in the art.

According to an embodiment apart from the clinical protocols for performing the analyses and the results of the analyses themselves, additional data could be transmitted comprising for example additional pieces of information relating to the user identification, information related to the performed analysis, GPS coordinates, date and place wherein the analysis was performed, etc.

According to an embodiment it will be further possible to access the diagnostic device (if connected to Internet) remotely. Each diagnostic device is identified univocally and, if connected to Internet, transmits its own ip to the belonging swarm server. In this way the diagnostic operator can plan the experiment (for example preparation of the samples and insertion of the sample-holder in the diagnostic device) and subsequently another (remote) operator can launch the analysis execution. The diagnostic devices could be used both singularly (as currently it happens for the existing apparatuses) and in 'swarm' mode, that is grouped in sets of instruments operating in cooperation.

Such grouping could take place both during the phase of identifying/tagging the instrument and/or the enabled operators, by assigning univocal passwords and recording the serial numbers of the instruments or other method apt to identify them, and by creating partitions at the level of the remote swarm server partitions so that all data coming from the instruments and/or operators belonging to the swarm are grouped and analysed jointly. This differs from the known art since this procedure was possible for physically contiguous instruments (same laboratory), and it is an extension at the level of data analysis of the 'portable' and remote analysis capability of the instrument. The advantage consists in the fact that different instruments, mobile on the territory, automatically make data to belong to a common partition without requiring an installation even at the software level whenever they change position as it currently happens.

The interface existing on the swarm-server even allows to plan the analyses, by sending requests to operators of diagnostic devices existing on the territory (which will receive a notification, and which could associate the results, once obtained, to such request).

It is further possible, upon request of the user of the swarm-server, to request a list of the operators of the diagnostic device existing near a determined area even if they do not belong to the same swarm, in order to be able to send them an analysis request.

According to an embodiment it will be possible to programme the automatic updating (for example a re-loading) of the script generating the meta-analysis under certain conditions (for example every total time, upon loading a new analysis concerning the subject pathogenic agent, etc.).

According to an embodiment inside the user interface (webapp) of the swarm-server an interpreter will be embedded, capable of performing script in a language suitable to the statistical processing (R, python or Julia). This interpreter preferably will be run in a virtual environment (to prevent that voluntarily or inadvertently the script corrupts the swarm-server) wherein all analyses performed by the swarm (and the analyses received by the swarm from associated swarms or loaded in other way) are present (with reading permission only). This allows implementing meta-analyses (which can generate, or not, HTML and PDF, even interactive, reports and graphs).

According to an embodiment these meta analyses can be accessed by the swarm manager and by all users enabled by him/her. People outside the swarm can access single meta-analyses or groups of meta-analyses by means of user name and password (generated and sent by means of a procedure started by the operator who created the meta-analysis).

A subject of the present invention is also a system suitable to perform the method according to the present invention. Such system comprises a first remote server (1) programmed for filing and updating a plurality of clinical protocols for clinical-diagnostic analyses and/or a plurality of results of clinical-diagnostic analyses;

one or more mobile devices (3) programmed for receiving and transmitting a plurality of protocols and results of clinical-diagnostic analyses;

one or more devices for clinical-diagnostic analyses (2) programmed for receiving from a mobile device a plurality of protocols and transmitting to a mobile device the results of the clinical-diagnostic analyses performed on said device, and wherein said server, said mobile devices and said devices for clinical-diagnostic analyses are interconnected by means of Internet or a local network. According to an embodiment such system comprises a second remote server (4) programmed for filing and updating a plurality of results of clinical-diagnostic analyses. The diagnostic devices of such system for example could be one or more devices for clinical-diagnostic analyses of rtq PCR (Quantitative reverse transcription PCR) or PCR lamp (Loop-mediated isothermal amplification), preferably said diagnostic devices will be portable devices.

According to a preferred embodiment the system server will include a software programmed for creating clinical protocols, creating interpreting protocols, creating protocols for meta-analysis, storing the obtained results, distributing the clinical protocols, distributing the interpreting protocols, distributing results of analyses and meta-analyses.

The figures of the present patent application show some preferred embodiments of the system or of the herein described method.

EXAMPLES

The description of a clinical protocol, which can be run on a specific analysis device which can be implemented according to the method of the present invention, will be shown hereinafter by way of example.

1. Control software specifications of a device for rtq PCR, PCR Lamp analyses and impedance measurements.

The Control software is an application for PC Windows, for the management and setting of the bioreader. The bioreader is a device for rtq PCR, PCR Lamp analyses and impedance measurements, connected to the PC by means of micro-USB USB-Serial cable. The bioreader, on board, has an embedded PC which apart from communicating with the subject software manages the execution of the protocol and the saving of the analyses data.

Bioreader Software Functions:

1. Creating modification of saving protocols for the Bioreader;

2. Loading protocol and configuring cartridge of samples in the Bioreader;

3. Reading and displaying of Analyses results;

1.1 Protocol Definition

Under protocol a series of steps is meant, wherein it is possible setting temperature, temperature gradient, constant temperature, temperature variation cycles, impedance measurements etc.

Two Types of Protocols first type nucleic acid amplification;

proteomic analyses.

1.1.1 Nucleic Acid Amplification Protocol

Two Variants thermal cycle or Real-Time isotherm or Lamp

Process divided into 3 phases:

Heating starting

Central portion, different in the Real-Time, wherein there are repeated cycles, and in the Lamp wherein the temperature is constant Thermal Cycle;

modules which can be repeated;

one module is time and temperature;

groupings at the first level of the modules and repetition of the blocks of modules;

Fine melting, a heating or a cooling can take place, in this phase it is important detecting the temperature as fluorescence parameter.

In the process duration images are shot and calculations on the pixels are performed.

The image shot involves a series of actions like switching-on of leds for lighting the cartridge, differentiated shooting with filters.

1.1.2 Proteomic Analysis Type Protocol

The protocol for the proteomic analysis has a different cartridge, with electric contacts at one end and a corresponding connector in the bioreader. From the software point of view the protocol for the proteomic analysis is an impedance measurement, there is no temperature control or image shooting.

LIST OF COMMANDS

The PC could communicate with the bioreader by means of serial or Bluetooth connection. Hereinafter there are the commands which the pc sends to the bioreader.

LOD

It loads the protocol in the bioreader. The protocol is an ASCII file with the sequence of the commands which the bioreader is going to perform, aboard the bioreader there is a control software which receives the protocol and transforms each command into a series of actions performed in the bioreader. Even in absence of a protocol the bioreader is capable of receiving a single command and activating the actions associated thereto during the phase of creating the firmware.

Once received the LOD command, the bioreader waits for receiving the list of commands of the protocol.

The END command shows to the bioreader the end of the list of commands of the protocol.

The LOD command does not verify the presence of a protocol in the bioreader, then it overwrites the protocol in case loaded into the bioreader.

END

End of protocol. The command has to be preceded by the LOD command and by the protocol instructions, in the contrary case it is interpreted as an escape. After this command the protocol is stored in the run memory of the bioreader and ready to be run. After the END command the bioreader receives the commands immediately, and then they are executed by the bioreader.

If during the loading of the protocol there is the need for a modification, it is necessary to end the current protocol and re-start with the LOD command, which then sets to zero the commands loaded previously.

An END per timeout is provided, in case after a LOD command and possible following commands 5 minutes elapse, the bioreader closes and cancels the protocol which is being loaded Answer

OK

The command has been received and the bioreader stores the loaded protocol

ERR Error number

An error has occurred, the error number makes reference to the list of errors wherein one can check the type of error and proceed with the correction

RUN

It runs the protocol immediately, if the protocol has not been loaded an error is generated.

The RUN command can be executed only in immediate mode, in case it is inserted in a protocol, that is after the LOD command, it is ignored.

If the RUN command is sent twice, or is sent while the protocol has already started and executed, it is ignored Answer

OK

The command has been received and the bioreader sends to execution the loaded protocol ERR Error number An error has occurred, the error number makes reference to the list of errors wherein one can check the type of error and proceed with the correction

RDD

It reads the results of the executive protocol. The command has the purpose of displaying in the software for PC and in the APP the analysis to be run on the bioreader. Upon each IMG instruction the firmware performs an acquisition and a processing of the cartridge image, the result of such processing is a number which represents the intensity of the measured fluorescence. The bioreader inputs the results for each sample for each analysis frequency in a memory buffer, which acts in FIFO mode wherein out is run by the RDD command The RDD command has no influence on saving the results of the whole analysis in the bioreader Answer List of results stored in the buffer of the bioreader ERR Error number An error has occurred, the error number makes reference to the list of errors wherein one can check the type of error and proceed with the correction

LSA

It lists performed and recorded analyses. Each analysis performed even partially in the bioreader is automatically saved in the permanent storage of the bioreader. For each analysis a directory is created with the analysis name, in the directory a file of the results and the raw images captured by the camera during the analysis are saved.

Answer

List of results

ERR Error number

An error has occurred, the error number makes reference to the list of errors wherein one can check the type of error and proceed with the correction RDS; Analysis Name It reads the results of the protocol performed and recorded in the permanent storage of the bioreader. The RDS command reads only the file of the results and not the raw images saved into the analysis directory Answer Reading of the file of the results and graphic and analytical display on the diagrammes ERR Error number An error has occurred, the error number makes reference to the list of errors wherein one can check the type of error and proceed with the correction

STP

It stops immediately the protocol which is being run in the bioreader. The restoring of an interrupted protocol is not provided, the results acquired until the stopping moment are saved for possible checks Answer

OK

The protocol has been interrupted

ERR Error number

An error has occurred, the error number makes reference to the list of errors wherein one can check the type of error and proceed with the correction IDA;AnalysisName IDA;PlantsPark Analysis identification. The string is used to identify the analysis, the same protocol can be performed several times. The analysis identification is used even as name for the directory of the permanent storage of the bioreader, wherein the file of the results and the raw images of each analysis are saved. The IDA command has no immediate execution, it is received only in LOD mode Analysis identification Answer

OK

ERR Error number

An error has occurred, the error number makes reference to the list of errors wherein one can check the type of error and proceed with the correction PRT;ProtocolNumber

PRT;RIC0000000000001

Id of the receipt to be executed

Id of the protocol to be run, it is a 16-character string. The string is used to identify the analysis protocol. Id protocol is used, apart from documenting the performed analysis, to check the compatibility to the cartridge inserted in the bioreader. The PRT command has no immediate execution, it is received only in LOD mode CRT;IdCartridge

CRT;CRT0000000000001

Id of the cartridge which has to be in the bioreader to run the protocol, it is a 16-character string Answer

OK

ERR Error number

An error has occurred, the error number makes reference to the list of errors wherein one can check the type of error and proceed with the correction The CRT1234567890 code is the passepartout and it does not generate alarm of the corresponding cartridge TMP;Temperature

TMP;68

It sends the cartridge at the shown temperature in the shortest possible time. The TMP command is executed immediately by the firmware of the bioreader, the bioreader checks the temperature so that there are no overshoots, once reached the temperature it is kept constant. The heating is interrupted even in case of end of protocol or interruption of protocol Answer

OK

ERR Error number

An error has occurred, the error number makes reference to the list of errors wherein one can check the type of error and proceed with the correction GRD;GradialSecond

GRD;0,2

It creates a gradient with the shown sloping

It creates a gradient with the shown sloping. The GRD command starts a temperature control with the designated gradient. The gradient can be positive heating or negative heating. If the gradient is not interrupted by a TMP I command the temperature is however stopped at limit values set in the firmware, the standard values are 97 for the maximum temperature and 10 for the minimum temperature Answer

OK

ERR Error number

An error has occurred, the error number makes reference to the list of errors wherein one can check the type of error and proceed with the correction TMR;Seconds

TMR;30

Timer waiting. After this command the firmware remains waiting for the time shown in seconds, decimals are not provided, but they are integer seconds, in case of minutes the conversion has to be made, for example 3 minutes are equal to 180 seconds. During the waiting period no command is executed, but the commands which are already being executed are not interrupted, if for example a thermal gradient command is executed, this continues without being influenced by the timer Answer

OK

ERR Error number

An error has occurred, the error number makes reference to the list of errors wherein one can check the type of error and proceed with the correction

IMG

It shots and processes an image of the cartridge. The image data are processed immediately and saved in the buffer of the ongoing analysis (see RDD command). The raw image is saved in the directory of the ongoing analysis. In case of the command in immediate mode, an image is shot and saved in the directory temp of the permanent storage of the bioreader Answer

OK

ERR Error number

An error has occurred, the error number makes reference to the list of errors wherein one can check the type of error and proceed with the correction WLS;Coordinates;Name;AnalysisType WLS A1 e.g. Sheep Dolly RT405

It identifies the cartridge well.

Answer

OK

ERR Error number

An error has occurred, the error number makes reference to the list of errors wherein one can check the type of error and proceed with the correction Reading and Displaying of the Analysis Results The Software has a view dedicated to reading the results of analyses, with a graph Cycles of Fluorescence The data reading can take place in two modes, Run and Stop.

In the Run mode the Pc remains connected to the bioreader and reads the data at a fixed time interval (ex 20 seconds), the graph on the Programme displays the data of each reading. The programme has a key for skipping the steps of the ongoing analysis.

In the Stop mode the data of the analysis concluded on the field are read.

Once concluded the analysis, a function transfers the results, both the raw ones and those processed in the PC, which has a system for filing and reading the results Two types of graph, Time intensity for displaying the reaction phases during the cycle(s)

A curve for each well, frequency

It is an Intensity temperature (or derivative) graph for the data collected in the melting phase A curve for each well, frequency Structure of file of the results The format of the results of the analyses is of ASCII or XML type, a standard format is looked for so that the system is capable of receiving different types of results.

Definitions

Executive Clinical Protocol:

Set of instructions which can be run by the clinical-diagnostic device

It is constituted by:

commands, apt to be executed by the hardware ("receipt")

parameters, inherent to analysis (such as for example number of samples, name of single samples, etc.)

It can include "high-level" or "low level" commands. The result of an executive protocol are raw data (recorded during execution)

Whereas the "receipt" is static, the parameters vary, and they are defined by the operator before launching the analysis execution. On the diagnostic device there is already a series of protocols for the most widespread kits on the market. The user could specify then a receipt containing only the "parameters" (name of receipt, number and name of samples, geolocalization etc.) and designating the executive protocol by means of a specific command (ex "PRT:Xylella 1.x")

In case the required protocol is not present, it will be downloaded from the device which in that moment acts as controller, or directly from Internet (if the diagnostic device is connected), otherwise the analysis execution will be inhibited.

Interpreting Protocols:

Set of instructions which are used for interpreting the results of the analyses performed by the clinical-diagnostic device.

Storage:

The raw data obtained from running the executive protocol are stored on the diagnostic device, and they can be provided as input to an interpreting protocol which will generate results and a report. The raw data, the results and the report are stored on the diagnostic device (which acts as file-server), thereto the user can access by means of the most common FTP/SCP clients.

Furthermore, upon the user request, the raw data/results/report, can be loaded in the user belonging swarm-server and they can be forwarded manually to a list of email addresses specified by the user (by means of the provided mobile application or by means of the web interface which is on the diagnostic device). Furthermore an automatic forwarding from the swarm-server to other swarm-servers, other email addresses or other servers (for ex. research networks) is possible, if on the user swarm-server rules for the automatic forwarding were defined (for example only for certain types of analysis/pathogens the swarm manager may want to forward the results to a specific research centre).

The raw data (and in case the results and report) then can be contemporarily stored on:

diagnostic device mobile device or PC connected (by means of any implemented communication protocol) to the diagnostic device belonging swarm-servers associated swarm-servers outer networks The diagnostic device periodically sends reports upon the use.

In case the space available on the inner storage is exhausting, it will provide automatically to compress (for example by means of zip compression algorithms) the analyses performed until that moment (and to disable, for example, the automatic saving of the images).

The diagnostic device keeps trace of all performed analyses. A device connected to the diagnostic device, connected by bluetooth, may require by means of a specific command the list of the analyses stored on the device.

Subsequently it may request a copy of the results of a specific analysis (report), the raw data (zip packet containing the historical series) or the analysis elimination. The mobile device can forward said analysis to the belonging swarm-manager and/or to a list of mail addresses. It can further delegate directly to the diagnostic device this procedure, by means of a specific command (if the diagnostic device is connected to Internet).

Commands

The commands are defined by means of a common interface included in a script accessible by the user, for example:

DefineCmd("LOAD", "^[a-zA-Z0-9]+$", {"SH":"INTERACTIVE"}, ["shell.load( )"], ['shell.state=="LOADING"', "'analysis.state=="LOADING"'], False)

The first passed parameter, "LOAD", is the command name

The second parameter "^[a-zA-Z0-9]+$", is a regular expression which allows to check in an immediate way if the arguments passed to the command are valid or not. In this case the regular expression is appropriate to any string including the characters a-z, A-Z, 0-9 and the spaces The LOAD:TEST command will be then valid, whereas LOAD:&TEST* will not.

the third parameter {"SH":"INTERACTIVE"}, defines a set of preconditions for executing the command. In this case the Shell (the interpreter of the commands) has to be in the "INTERACTIVE" state, otherwise the command will not be executed the fourth parameter ["shell.load( )"] is a vector representing the state transitions of the various demons/modules which constitute together the onboard software of the diagnostic device. In this case a shell.load( ) function will be recalled which performs a transition of the interpreter state from "INTERACTIVE" to "LOADING"

the fourth parameter, ['shell.state=="LOADING"', "'analysis.state=="LOADING"'], are the output conditions. Considering that one wants to keep the maximum level of interactivity and in asynchronous way, it is not conceivable to lock the input/output or the execution of some sub-processes until the end of the body of the requested command. The interpreter of the commands stores these output conditions and it evaluates them continuously. In the moment wherein they are met, it will pass to execute the subsequent command in receipt the last argument (in this case "False") tells if the requested one is a real command or a parameter of the analysis. In case it is a parameter of the analysis (and then set up to "True") it will be run as soon as met by the interpreter, whereas if it is a command, it will be run in the right moment after having launched the RUN command The same script implements an EvaluateCommand function (InputString, Commands), thereto a string (the input inserted by the user, which can be received by any I/O demon), and the vector of the stored commands pass as input.

This function returns a "Command" object.

If for example the user inserts the string "LOAD:TEST1", EvaluateCommand("LOAD:TEST1", VectorCommands), it will return a so-structured Command object:
Command.name="LOAD"
Command.arg="TEST1"
Command.context={"SH":"INTERACTIVE"}
Command.transition=['shell.state=="LOADING"', "'analysis.state=="LOADING"']
Command.parameter=False
Command.complete=False The interpreter, at the end of the execution of transactions, and at the end of the body of the associated function, will set Command.complete=True, and will insert the command in a vector of the commands executed successfully (the list thereof will be reported in the final report)

This allows simplifying radically the implementation of new commands, even if by the user, when in the main cycle of the interpreter only the main logic of the command will have to be inserted, considering that all formal controls and state transitions were performed in advance The logic of the "LOAD" command, in the main cycle of the interpreter, is made in the following way
Def ExecuteCommand(Command):
if Command.name=="LOAD":
SetupAnalysis(Command.arg)

As it can be seen it is not necessary to apply any control on the input correctness. This even allows the end user, capable of developing in the language used to implement the interpreter, to implement new, initially not provided, commands.

High-Level Commands

For certain types of analysis (rtPCR and lampPCR) the diagnostic device implements a series of high-level commands like the following ones:
AMPLIFICATION: 65; 1200

This command brings the cartridge at 65 degrees, and keeps this temperature for 1200 seconds before performing the subsequent command. Once reached the target temperature, the acquisition of the intensities detected at the single samples (by coordinating automatically the camera and the leds corresponding to the set filters) is started parallelly
CYCLE:20;92;60;56;60;35;60

This command defines the cycles for implementing an analysis of real-time PCR type. In this example 20 cycles will be performed, each one thereof constituted by 3 passages:
1) first passage at 92 degrees for 60 seconds
2) second passage at 56 degrees for 60 seconds
3) third passage at 35 degrees for 60 seconds Automatically, at the end of the third passage, and before passing to the subsequent cycle, the capture of the intensities will be performed (by coordinating automatically the camera and the leds associated to the defined filters).

If the number of cycles is ended, the subsequent command in receipt will be executed In substance, the high-level commands, devised for implementing on the diagnostic device the analyses of rtPCR and LAMP type, coordinate automatically all inner components existing in the device (in case of peltier module example, different sets of leds for each filter, camera, I/O device), and perform state transitions rigidly defined for the type of performed analysis (for example, in a LAMP analysis no amplification could be performed after a melting curve)

Low-Level Commands

They allow to dialogue directly with the hardware inside the device
es.
PLT TMP:65
it shows to the peltier to go at 65 degrees.
LED BLUE ON
It switches on the blue led
LED BLUE PWR: 50
it sets the Power of the blue led at 50%
TMR:100
it sets a timer of 100 seconds, at the end thereof the subsequent command will be executed When receipts are used including low-level commands, state transitions are not defined. The user can execute any command in any order.

The execution can be distributed between a controller device and the diagnostic device (the controller device could launch the PLT TMP:65 command and wait for that temperature has been really reached, before sending another command)

In this way the user can implement analyses which were not initially provided, but which, in order to be executed, require hardware components already present on the diagnostic device (ex ELISA)

Interactive mode

Upon starting the onboard software an empty receipt is loaded. The user can insert commands in interactive way. All executed commands are logged (together with the raw data coming from the thermal module and from the camera), and they will be visible in the report generated upon leaving the interactive mode.

Filters

Not applicable

Amplification

During the amplification phase in a lamp analysis (or at the end of the last passage of a cycle in a real-time PCR analysis), if wells with overlapped excitation/emission frequencies were defined, alternatively the intensities on each filter will be taken Melting Curve Considering that the diagnostic device is devised even for multiplex analyses, in case wells with overlapped excitation/emission frequencies were defined, the melting curve will be repeated on each one of the conflict filters, singularly (in order to have the greater number of intensities recorded for each temperature)

Raw data

They are the data recorded by the sensors existing on the diagnostic device.

They are saved on text file .csv (and in case serialized in other not-proprietary formats such as json, xml, rdml).

For the intensity data, apart from the timestamp, also temperature, target temperature, filter used in that moment are stored. These are all useful data to be able then to apply an automatic interpreting protocol Results/Interpreting protocol To each sample a result of POSITIVE, NEGATIVE, INDETERMINATE type will be associated These results are obtained by applying automatically an interpreting protocol on the raw data.

The user/swarm manager, can create and store in his/her swarm-server new interpreting protocols, under the form of functions in a suitable scripting language (R, Julia, Python or others) to receive as input a csv formatted according to the interface provided by us and to emit as output a string, representing a vector, with value "POS", "NEG", "IND"

Before executing such script a static control is performed (for example to verify that the script uses only the allowed libraries and not for example libraries allowing the access to other resources on the diagnostic device).

The user of the swarm-server can further apply different interpreting protocols to a same set of the raw data, thus by producing potentially different results (each result is saved by keeping trace both of the parameters of the analysis and of the used executing protocol and of the applied interpreting protocol).

It can further modify manually the (positive/negative/indeterminate) results based upon its experience.

Whenever the results of an analysis are updated/modified or whenever a new interpreting protocol is applied to a set of the already previously analysed raw data, all users/actors who had received the initial results will receive even a notification with the new results.

Communication protocol

The interpreter of the commands does not receive the input directly from a communication channel, as it can be bluetooth, tcp/ip, serial etc., but it reads on a local database/dictionary (such as example Redis) all keys of "list" type beginning with "InputChannel.*"

For each detected list (for example "InputChannel.Bluetooth", or "InputChannel.Telnet") it will extract the first inserted element (the list is treated as a FIFO), and it will evaluate it (by passing the string to the function transforming the string into a command, for example EvaluateCommand).

As far as the output is concerned, each outgoing message will be appended to each found key of the "OutputChannel.*" type.

The user, capable of programming in any language therefor on the device a compiler/interpreter and the required libraries are available, can implement a server/demon, which provides to read from another I/O channel which was not initially provided, it can create a key of the "InputChannel.ChannelName" type, and add the received input in such list.

If it wanted for example to connect a usb keyboard, it should create a programme reading the data coming as input therefrom and append them to a "InputChannel.Keyboard" key.

The interpreter will read automatically even the so-defined flow of input.

All general data (ex temperature, intensity) are appended in the output lists. In this way, a connected client (telnet, excel sheet by means of a plugin, general bluetooth terminal, mobile application provided by us) will receive in real time the raw data, which he/she could display/manage in the provided ways or in alternative ways A mobile or fixed device can connect to the diagnostic device even subsequently the launch of the analysis execution, by acting then as "monitor", and being capable to interact only on some parameters.

For example the analysis can be launched by a PC directly connected by means of ethernet connection to the diagnostic device, or by remote PC connected to the diagnostic device by means of internet, and subsequently the execution thereof can be monitored by connecting by means of the provided mobile app (bluetooth) to display the graphs of the course of temperatures and intensities. The mobile application is capable of identifying the execution state and then it will expose in the user interface only some functionalities (it will not be possible, up to the end of the execution to set new analyses, but it will be possible to interrupt ongoing analyses, or extend the duration in some phases).

The mobile application can further perform an accelerated "replay" of previous analyses (if it has downloaded from the diagnostic device the raw data of temperature and intensity).

With the proposed implementation a plugin for Microsoft Excel is further provided which allows to connect any calculation excel sheet to the diagnostic device. This allows the laboratory operator to avoid learning from scratch a new software.

Furthermore it allows him/her to have directly in the calculation sheet (often favourite instrument to proprietary softwares) the data to be analysed.

The invention claimed is:

1. A method for management of clinical protocols configured to run on devices configured to perform clinical and diagnostic analysis and the results obtained by said devices comprising the following steps:
    a) storing, on a first remote server, and periodically updating a plurality of clinical protocols configured to run on devices configured to perform clinical and diagnostic analysis;
    b) transmitting, from said first remote server to a mobile device, one or more of said protocols;
    c) transmitting, from said mobile device to a device configured to perform clinical and diagnostic analysis, the one or more of said protocols, wherein the device configured to perform clinical and diagnostic analysis is further configured to operate in a first mode, the first mode comprising a swarm mode based on one or more partitions created at said first remote server, wherein said devices operating in the swarm mode are grouped by assigning univocal passwords and recording instrument serial numbers;
    d) transmitting, from said device configured to perform clinical and diagnostic analysis to said first remote server, an ip address so as to identify said devices configured to perform clinical and diagnostic analysis univocally on a network;
    e) performing a clinical-diagnostic analysis according to the protocol transmitted;
    f) transmitting, from said device configured to perform clinical and diagnostic analysis to said mobile device, results of the clinical-diagnostic analysis obtained at point d); and
    g) transmitting, from said mobile device to said first remote server or to a second remote server, said results based on one or more predefined command rules configured for automatic forwarding for a specified type of analysis.

2. The method of claim 1 wherein said devices configured to perform clinical-diagnostic analyses comprise portable devices.

3. The method of claim 1 wherein in said transmission steps b), c), f) and/or g) transmitted data comprising one or more of said protocols and the results are encrypted.

4. The method of claim 1 wherein in said transmission steps c) and/or g) additional data including information relating to user identification, information related to the performed analysis, GPS coordinates or date and place where the analysis was performed are transmitted.

5. The method of claim 1 wherein access to said protocols and to said results stored on said first or second remote servers are protected by password.

6. The method of claim 1 wherein in said transmitting steps b), c), f) and/or g) transmitted data comprising one or more of said protocols and the results are transmitted via email, SMS, instant messaging services and/or applications for a smartphone.

7. The method of claim 1 wherein said device configured to perform clinical and diagnostic analysis comprises a device configured to perform an analysis of rtq PCR (Quantitative reverse transcription PCR) or PCR lamp (Loop-mediated isothermal amplification).

8. The method of claim 1 wherein said first remote or said second remote servers, said devices configured to perform clinical-diagnostic analysis, and said mobile device are connected therebetween by Internet.

9. The method of claim 1 further comprising
h) storing, on said first remote server, a plurality of protocols interpreting analyses configured to run on said devices configured to perform clinical-diagnostic analyses;
i) transmitting, from said first remote server to said mobile device, one or more of said interpreting protocols;
j) transmitting, from said mobile device to said devices configured to perform clinical-diagnostic analyses, one or more of said interpreting protocols for a clinical-diagnostic analysis; and
k) interpreting results of the clinical-diagnostic analysis according to the interpreting protocol transmitted at point j).

10. The method of claim 9 wherein said results comprise raw data in text/csv format, json, xml or rdml server configured to be interpreted by said interpreting protocols.

11. The method of claim 1 wherein said first remote server or said second remote server is connected to said devices configured to perform clinical-diagnostic analysis by Internet.

12. The method of claim 1 wherein said first remote server or said second remote server acts with respect to said devices configured to perform clinical and diagnostic analysis as a swarm server.

13. A system for management of clinical protocols configured to run on devices configured to perform clinical and diagnostic analysis and the results obtained by said devices comprising:
a first remote server programmed for filing and updating a plurality of protocols for clinical-diagnostic analyses and/or a plurality of results of clinical-diagnostic analyses;
one or more mobile devices programmed for receiving from said first remote server and transmitting the plurality of protocols and results of clinical-diagnostic analyses; and
one or more devices configured to perform clinical-diagnostic analyses programmed for receiving from a mobile device the plurality of protocols and transmitting to the mobile device the results of the clinical-diagnostic analyses performed on said device configured to perform clinic-diagnostic analyses, the results transmitted based on one or more predefined command rules configured for automatic forwarding for a specified type of analysis, wherein
said first remote server, said one or more mobile devices, and said devices configured to perform clinical-diagnostic analyses are interconnected by Internet,
the devices configured to perform clinical-diagnostic analyses are further configured to operate in a first mode, the first mode comprising a swarm mode based on one or more partitions created at said first remote server, said devices operating in the swarm mode are grouped by assigning univocal passwords and recording instrument serial numbers, and
the devices configured to perform clinical-diagnostic analyses are further configured to transmit an ip address to the first remote server so as to identify said devices configured to perform clinical-diagnostic analyses univocally on a network.

14. The system of claim 13 further comprising a second remote server programmed for filing and updating the plurality of results of clinical-diagnostic analyses.

15. The system of claim 13 wherein said one or more devices configured to perform clinical-diagnostic analyses are configured to perform analyses of rtq PCR (Quantitative reverse transcription PCR) or PCR lamp (Loop-mediated isothermal amplification).

16. The system of claim 13 wherein said one or more clinical-diagnostic analyses devices comprise portable devices.

17. The system of claim 13 wherein said one or more mobile devices are programmed so as to transmit by a touch screen interface operating instructions to said clinical-diagnostic analyses devices.

18. The system of claim 13 wherein said first remote server comprises a software programmed for creating clinical protocols, creating interpreting protocols, creating protocols for meta-analysis, storing the obtained results, distributing the clinical protocols, distributing the interpreting protocols, and distributing results of analyses and meta-analyses.

19. The system of claim 13 wherein said one or more devices configured to perform clinical-diagnostic analyses are programmed receive, store, and transmit to said first remote server and/or to said one or more mobile devices the results of the clinical-diagnostic analyses as raw data.

20. The system of claim 13 wherein said first remote server is connected to said one or more mobile devices and to said devices configured to perform clinical-diagnostic analyses by Internet so that said first remote server is configured as a swarm server.

* * * * *